(12) United States Patent
Nishida (10) Patent No.: US 10,308,725 B2
(45) Date of Patent: Jun. 4, 2019

(54) CHELATE COMPOUNDS AND THEIR SYNTHETIC METHODS

(71) Applicant: DISEASE ADSORPTION SYSTEM TECHNOLOGIES CO., LTD., Kanazawa-shi, Ishikawa (JP)

(72) Inventor: Yuzo Nishida, Kanazawa (JP)

(73) Assignee: DISEASE ADSORPTION SYSTEM TECHNOLOGIES CO., LTD., Kanazawa-shi, Ishikawa (JP)

( * ) Notice: Subject to any disclaimer, the term of this patent is extended or adjusted under 35 U.S.C. 154(b) by 0 days.

(21) Appl. No.: 15/324,904

(22) PCT Filed: Sep. 29, 2015

(86) PCT No.: PCT/JP2015/077468
§ 371 (c)(1),
(2) Date: Jan. 9, 2017

(87) PCT Pub. No.: WO2016/052488
PCT Pub. Date: Apr. 7, 2016

(65) Prior Publication Data
US 2017/0210828 A1    Jul. 27, 2017

(30) Foreign Application Priority Data

Sep. 29, 2014 (JP) ................. 2014-198609

(51) Int. Cl.
| | | |
|---|---|---|
| C08B 37/08 | (2006.01) | |
| C07H 15/18 | (2006.01) | |
| A61K 31/722 | (2006.01) | |
| G01N 33/20 | (2019.01) | |
| B01D 21/01 | (2006.01) | |
| A61K 9/00 | (2006.01) | |
| A61K 9/06 | (2006.01) | |

(52) U.S. Cl.
CPC .......... *C08B 37/003* (2013.01); *A61K 9/0014* (2013.01); *A61K 9/06* (2013.01); *A61K 31/722* (2013.01); *B01D 21/01* (2013.01); *C07H 15/18* (2013.01); *G01N 33/20* (2013.01)

(58) Field of Classification Search
CPC ........................... C08B 37/003; A61K 31/722
See application file for complete search history.

(56) References Cited

U.S. PATENT DOCUMENTS

| | | |
|---|---|---|
| 4,424,346 A | 1/1984 | Hall et al. |
| 5,300,628 A | 4/1994 | Honda |
| 2013/0292337 A1 | 11/2013 | Nishida et al. |

FOREIGN PATENT DOCUMENTS

| | | |
|---|---|---|
| EP | 2664333 A | 11/2013 |
| WO | WO-2012/096183 A1 | 7/2012 |

OTHER PUBLICATIONS

J. Wahlberg et al. (ed.), Management of Positive Patch Test Reactions, 2003, Springer-Verlag Berlin Heidelberg, p. 81. (Year: 2003).*
Soliman et al., Mussel-inspired Chitosan Nanogels with Enhanced Stability and Mucoadhesion for Drug Delivery, 2012 Controlled Release Society Annual Meeting Abstract, held Jul. 15-18, 2012. (Year: 2012).*
Kim et al., Biomater. Sci., 2013, 1, p. 783-790. (Year: 2013).*
Yalinca et al., J. Appl. Polym. Sci., 2012, 125, p. 1493-1505. (Year: 2012).*
Extended European Search Report dated Mar. 27, 2018.
O Wacker et al, "von D-Glucopyrano-(cis-2', 1'-c)-1, 2, 3, 4-tetrahydroisochinolinen", Hevletica Chimica Acta, vol. 50, No. 8, Jan. 1, 1967, pp. 2481-2490, XP055424082.

* cited by examiner

*Primary Examiner* — Jonathan S Lau
(74) *Attorney, Agent, or Firm* — Yokoi & Co., U.S.A.; Toshiyuki Yokoi (57) ABSTRACT

A chelate compound wherein a chelate-forming moiety is attached to a base compound having an amino group and at least a part of the amino group is in the form of a halide salt. A specific example of the halide salt is hydrochloride. As the base compound, a chitosan having a glucosamine skeleton is preferred. Also, chitosan beads are usable. The chelate compound is produced by reacting the base compound having an amino group with an aldehyde group of an aromatic cyclic compound, aromatic cyclic compound having at least a functional group capable of forming a chelate and the aldehyde group, to form a Schiff base, reducing the Schiff base with a reducing agent and then treating with a hydrohalogenic acid (hydrochloric acid).

1 Claim, 8 Drawing Sheets

CHELATE COMPOUNDS AND THEIR SYNTHETIC METHODS

TECHNICAL FIELD

The present invention relates to chelate compounds in which a chelate-forming moiety has been introduced into a base compound having amino groups, such as chitosan, and to their synthetic methods, and relates in particular to novel chelate compounds which have been rendered to be water-soluble through treatment with hydrochloric acid, and to their synthetic methods.

BACKGROUND ART

Chitosan is a β-1,4-linked polymer of glucosamine (2-amino-2-deoxy-β-D-glucose), and is obtained by deacetylation of chitin (poly-N-acetyl glucosamine), which is abundant by-product in the crab and shrimp processing industries. Chitosan has long been indicated as exhibiting antibacterial/antioxidant action, and may be valuable resource of high utility.

The inventors of the present application have also noted the usefulness of chitosan, and previously developed a water-insoluble polymer iron chelating agent which can capture selectively biologically unstable iron (i.e., NTBI), and proposed that chelates insoluble in water are not drawn into metabolic processes in the body (see Patent Document 1).

Patent Document 1 discloses a water-insoluble polymer iron chelating agent in which a phenol based chelating agent of specific structure is bonded by chemically stable —NH—$CH_2$— bonds to a chitosan chain, and also disclosed a method for capturing iron ions, using the polymer iron chelating agent in question.

PRIOR ART DOCUMENT

Patent Document

Patent Document 1: PCT Domestic Republication WO 2012/096183

SUMMARY OF THE INVENTION

Problems to be Solved by the Invention

The polymer iron chelating agent disclosed in the aforementioned Patent Document 1 has the advantage that, being water-insoluble, the compound is not drawn into metabolic processes in the body, but depending on the application, water solubility may be required in some instances.

For example, in order to use these compounds in antibacterial filters for air conditioning systems, toothpaste, and dermal mediations, it is preferable for chitosan to be water-soluble. Water-soluble chitosan readily forms a hydrogel in aqueous solution, which may be valuable for the aforementioned applications.

Solubilization and antimicrobial transformation of natural chitosan can typically be achieved through quanternization of the amino groups of chitosan. Quanternized chitosan is obtained by quanternization of the amino group at the C-2 position. However, it is necessary to use a halogenated alkyl agent during the quanternization, and there is a risk that such agents are toxic.

The present invention has as an object to provide chelate compounds which are highly safe and are applicable in various uses, as well as to provide the synthetic methods. A further object of the present invention is to provide chelate compounds of various forms, such as water-soluble and water-insoluble forms for various applications, as well as their synthetic methods.

Means for Solving the Problems

In order to achieve the aforementioned objects, the chelate compounds by the present invention are characterized in that a chelate-forming moiety is bonded to a base compound having amino groups, and at least some of the amino groups are halide salts.

The synthetic method for chelate compounds of the present invention is characterized in that the aldehyde group of an aromatic cyclic compound able to form a chelate is present, and the aldehyde group is reacted with a base compound having amino groups, to form a Schiff base, which is then reduced by a reducing agent, and treated with hydrohalic acid.

The chelate compounds of the present invention are synthesized by a procedure different from quaternization of amino groups, and is characterized in that the chelate compounds, while having various functionalities such as an iron removal function, have no toxicity. Moreover, through selection of the base compound, various chelate compounds for particular applications are provided.

For example, by using chitosan as the base compound, a water-soluble chelate compound may be obtained, and water-soluble chelate compounds readily form hydrogels in aqueous solution, giving many additional utilization. Also, by employing chitosan of water-insoluble bead form as the base compound, it is possible to obtain completely novel chelate compounds that have not been encountered to date.

Meanwhile, according to the synthetic method of the present invention, a chelate compound can be converted to the form of a halide salt through reduction by a reducing agent, followed by treatment with a hydrohalic acid (e.g., hydrochloric acid). Typically, during formation of a Schiff base or reduction by a reducing agent, residual unreacted Schiff base compounds or reducing agent used can be toxic. For these reasons considerable time and effort are required to wash these out. Additionally, it is necessary to use large amounts of the reducing agent in order to completely delete the unreacted Schiff base. Treatment with the aforementioned hydrohalic acid (hydrochloric acid) is effective in solving these problems, and through treatment with hydrochloric acid for example, any unreacted Schiff base compounds and reducing agent will be broken down and completely be eliminated within a short time.

Advantageous Effects of Invention

According to the present invention, it is possible to provide chelate compounds with which use in various applications is possible. Moreover, it is possible to provide chitosan chelate compounds of an appropriate form, such as a water-soluble chitosan chelate compound, a chelate compound in the form of water-insoluble beads, for various applications. Further, the synthetic method of the present invention has the effect that unreacted Schiff base compounds or reducing agent can be completely eliminated within a short time, further enhancing the safety of the chelate compounds obtained thereby.

DESCRIPTION OF THE EMBODIMENT

The synthetic methods of chelate compounds in which the present invention is implemented, are described in detail below.

The chelate compounds of the present invention have a chelate-forming moiety bonded to a base compound that has amino groups, at least some of the amino groups being halide salts.

Some compounds having amino groups can be employed as the base compound, including the both high-molecular compounds and low-molecular compounds. The compound having a glucosamine skeleton is preferred, the most preferred compound being chitosan. It is possible to use chitosan of various molecular weights, and of several forms such as flake form or bead form.

The chelate compound of the present invention has a chelate-forming moiety bonded to the base compound via an amino group. Functions as a chelating agent are effected by this chelate-forming moiety. The chelate-forming moiety is an aromatic ring (e.g., a phenol derivative) having a functional group that can form a coordinate bond with a metal, such as a hydroxyl group. Structures shown in Formulas 1-4, for example, can be cited as specific structures.

In an example showing the structure in Formula 1, the chelate-forming moiety is an aromatic ring having two hydroxyl groups situated at ortho-positions, in which a coordination bond is formed to give a stable coordination structure of a 5-membered ring with a metal ion (e.g., an iron ion).

[Formula 1]

In an example shown in Formula 2, the chelate-forming moiety is an aromatic ring having one hydroxyl group and one carboxylic acid group situated at ortho-positions, in which a coordination bond is formed in such a way that stable coordination structure of a 6-membered ring is formed with a metal ion (e.g., an iron ion).

[Formula 2]

In an example shown in Formula 3, the chelate-forming moiety is an aromatic ring having a carboxylic acid group bonded via an amino group to one hydroxyl group situated at ortho-positions, with which chelation of a metal ion (e.g., an iron ion) by a stable coordination structure to form one 5-membered ring and one 6-membered ring.

[Formula 3]

In an example shown in Formula 4, the chelate-forming moiety is an aromatic ring having one hydroxyl group, and two functional groups (carboxylic acid groups bonded via amino groups) situated at ortho-positions to either side, making it possible to increase the number of metal ions that can be chelated per single chelate-forming moiety.

[Formula 4]

A significant feature of the chelate compound by the present invention, besides having the aforedescribed structures, is that at least some of the amino groups take the form of halide salts. Doing so various advantages, such as solubilization in water, are conferred to chelate compounds.

Possible halide salts include, in addition to hydrochloride, salts such as HBr, HI, and HF. In the applications such as oral ingestion or medical use, for example, the salt would be limited to hydrochloride for safety reason.

An outline of the configuration of the chelate compound of the present invention will be illustrated; embodiments of specific chelate compounds in which the present invention is implemented are described below.

The chelate compound shown by Formula 5 has a natural high polymer known as chitosan as the base compound. The chitosan used as the base compound is a commercially available compound (with a molecular weight of 90,000 or less), chitosan with a molecular weight of 54,000, and also chitosan with a molecular weight of 35,000.

[Formula 5]

In the chelate compounds shown by Formula 5, the substituent group on the aromatic ring is a functional group that can form a coordination bond as described previously, and therefore at least one of $R_1$, $R_2$, $R_3$, $R_4$ and $R_5$ in the formula is a hydroxyl group, the others being any selected from a hydrogen atom, a hydroxyl group, a carboxylic group, and an alcohol group.

Examples of specific combinations of substituent groups are as follows. In the combination examples, compound names for identifying the compounds are appended for convenience.

Example 1: $R_1=R_2=OH$, $R_3=R_4=R_5=H$ (chelate compound A-1)
Example 2: $R_1=R_4=R_5=H$, $R_2=R_3=OH$ (chelate compound A-2)
Example 3: $R_1=R_2=R_3=OH$, $R_4=R_5=H$ (chelate compound A-3)
Example 4: $R_1=R_3=OH$, $R_2=R_4=R_5=H$ (chelate compound A-4)
Example 5: $R_3=OH$, $R_1=R_2=R_4=R_5=H$ (chelate compound A-5)
Example 6: $R_1=R_4=R_5=H$, $R_2=COOH$, $R_3=OH$ (chelate compound A-6)
Example 7: $R_1=R_4=R_5=OH$, $R_2=COOCH_3$, $R_3=OH$ (chelate compound A-7)
Example 8: $R_1=OH$, $R_2=OCH_3$, $R_3=R_4=R_5=H$ (chelate compound A-8)
Example 9: $R_1=R_4=R_5=H$, $R_2=OCH_3$, $R_3=OH$ (chelate compound A-9)

Whereas chitosan is insoluble in water, the chelate compounds indicated by Formula 5 having chitosan as the base compound are water-soluble, and are considered to be useful not only in eliminating dust, but also eliminating pathogens and viruses, when these compounds are added in the filters for vacuum cleaners, air conditioning systems, and air purifiers. Because the chelate compounds of the present invention exhibits an iron removal function, they should act to clean the teeth, when added in the toothpaste.

Further, the water-soluble chitosan indicated by Formula 5 has the characteristic of forming a hydrogel, and was found to exhibit the function to remove phosphoric acid. The medical effects afforded by hydrogels should be due to the metal ion chelating action.

Of the chelate compounds obtained, the chelate compound A-6, the chelate compound A-9, and a hydrogel of the chelate compound A-2 readily form precipitates in aqueous solution with phosphate ions, diphosphate ions, polyphosphate ions, molybdate ions, and bichromate ions, and can therefore be used to eliminate phosphate ions and others. In addition to above, the chelate compounds of the present invention, when bonded to an iron ion, strongly bind with phosphate ions and homologues (diphosphate, polyphosphate), and also with hydrogen peroxide, and thus efficiently eliminate these compounds.

While there are a number of organic compounds known to date that form a precipitate with phosphate ions, the water-soluble chelate compounds of the present embodiment have chitosan as the matrix, and therefore are considered to be safe to the human body, and can be utilized as an oral drug for phosphate ion removal. While phosphate ion is essential to the body, excessive levels can be harmful, and have been indicated to be dangerous to dialysis patients, for example. For patients suffering from chronic kidney disease, dialysis is crucial for supporting life, and the development of drugs that can efficiently remove phosphate ion is a crucial issue. At present there are some drugs available commercially including lanthanum carbonate, but safety of these compounds have been pointed out. The water-soluble chelate compounds of the present embodiment give no problems in safety.

In nowadays, phosphate ion is added as a preservative to many food products, but phosphate ion is a regulated additive. In recent years, to avoid phosphate ion regulations, diphosphoric acid (pyrophosphoric acid) and polyphosphoric acid are used in place of phosphate ion, but is it desirable to avoid these as much as possible as well. The chelate compounds of the present embodiment form precipitates with diphosphoric acid (pyrophosphoric acid), and polyphosphoric acid, making their removal to be possible. Molybdenic acid, vanadic acid, and bichromic acid, are compounds shown to be toxic substances to the body, and the chelate compounds of the present embodiment are capable of removing these toxic substances as well.

As to description of the medical effects, there have been a number of water-soluble chitosan derivatives known to date, and these have been indicated to have numerous efficacies (see, e.g., Domestic Republication WO 2012/105685); the chelate compounds of the present embodiment are thought to have comparable effects. The efficacy of hydrogels of the chelate compounds includes the ability to serve as wound therapy, as well as effects in relieving pain and inflammation and in cooling, due to the fact that the main component in the hydrogels is water.

Nanogel formation is a special example of a hydrogel, and formation of nanogels was observed for chelate compounds of the present embodiment (e.g., chelate compound A-6).

Further, when aqueous solutions of the water-soluble chelate compounds of the present embodiment (e.g. chelate compound A-2) are left to stand, a film forms, and the chelate compound constituting the film binds strongly with iron ions, and thus films obtained in this way can be used for iron detection. As an example of such uses, in addition to qualitative use by simply immersing the film in a solution to be detected, and determining the presence of iron ions from a change in color, there can also be cited quantitative uses, by examining the colored portion of the film with spectroscopic methods, and quantifying the iron ions through comparison with a standard density solution.

Next, examples of compounds where bead-shaped chitosan is used as the base compound are indicated by Formula 6. The crosslinking structure in Formula 6 will not be discussed.

[Formula 6]

In Formula 6, the substituent groups $R_1$, $R_2$, $R_3$, $R_4$ and $R_5$ on the aromatic ring are the same as in the chelate compounds indicated in Formula 5 previously. Examples of combinations of specific substituent groups follow. In the combination examples, compound names for identifying the compounds are appended for convenience.

Example 1: $R_1=R_2=OH$, $R_3=R_4=R_5=H$ (chelate compound B-1)
Example 2: $R_4=R_4=R_5=H$, $R_2=R_3=OH$ (chelate compound B-2)
Example 3: $R_1=R_2=R_3=OH$, $R_4=R_5=H$ (chelate compound B-3)
Example 4: $R_1=R_3=OH$, $R_2=R_4=R_5=H$ (chelate compound B-4)
Example 5: $R_3=OH$, $R_1=R_2=R_4=R_5=H$ (chelate compound B-5)
Example 6: $R_1=R_4=R_5=H$, $R_2=COOH$, $R_3=OH$ (chelate compound B-6)
Example 7: $R_1=R_4=R_5=H$, $R_2=COOCH_3$, $R_3=OH$ (chelate compound B-7)
Example 8: $R_1=\!=\!-OH$, $R_2=\!=\!-OCH_3$, $R_3=R_4=R_5=\!=\!-H$ (chelate compound B-8)
Example 9: $R_1=R_4=R_5=H$, $R_2=OCH_3$, $R_3=OH$ (chelate compound B-9)

The bead-shaped chitosan is a water-insoluble substance consisted of crosslinked chitosan, which is obtained commercially (e.g. CHITO PEARL™ from Fujibo Corp.). Processing of bead-shaped chitosan to give functionality has not been done to date, and an iron removal function imparted in the present invention is notable.

It is thought that when bead-shaped chitosan is used as the base compound, the chelate-forming moieties were bound to the surfaces of particles, and amino groups on the surfaces are converted to halide salts (hydrochloride).

Chelate compounds obtained using bead-shaped chitosan as the base compound are insoluble in water, and therefore are easily separated from a reaction system, giving them with exceptional ease of handling. The bead-shaped chelate compounds of the present embodiment have an iron removal function, a phosphate ion removal function, and a removal function of toxic substances such as bichromic acid, and can therefore be used for purification of the water.

As the chelate compounds containing bead-shaped chitosan are not particularly required to be water-soluble, therefore use of these compounds is possible without convertion to halide salts; however, conversion to a halide salt (hydrochloride) is advantageous in that impurities such as reducing agents can be quickly removed during the synthesis process.

Formula 7 and Formula 8 are examples of chelate compounds that employ low-molecular weight base compounds. Formula 7 is a chelate compound that has glucosamine as the base compound, and Formula 8 is a chelate compound that has histidine as the base compound. These chelate compounds can be used as reagents for quantitative testing of iron ions, or for detection of biologically unstable iron (NTBI) in cells or tissue.

[Formula 7]

[Formula 8]

In Formulas 7 and 8, the substituent groups $R_1$, $R_2$, $R_3$, $R_4$ and $R_5$ on the aromatic ring are the same as in the chelate compounds indicated in Formula 5 previously.

Not only the chelate compounds of the present invention have the advantages mentioned previously, a further advantage associated with the treatment for conversion to a halide salt (particularly hydrochloric acid treatment) during synthesis is that product exhibiting excellent safety can be synthesized efficiently with minimal impurities. The synthetic methods for the chelate compounds of the present invention are described below.

To synthesize the chelate compounds of the present invention, a base compound having amino groups is reacted with the aldehyde groups of an aromatic ring compound having functional groups able to form a chelate Formula 9 shows a synthesis process for a chelate compound of the present invention. Here, an example in which the base compound is chitosan, and is converted to a hydrochloride by hydrochloric, the treatment being described.

[Formula 9]

Synthesis is basically a procedure involving a condensation reaction of aldehyde groups and amine groups present in chitosan (formation of a Schiff base, —HC=N—R), and reduction of the double bond to give the single bond, —CH$_2$—HNH—R. The chelate-forming site is introduced through the formation of a Schiff base.

Important factors in the synthesis processes are the ease of formation of a Schiff base, its stability, ease of reduction of the Schiff base, and the stability of the reduced compound. When a chelate compound of the present invention will be used as a medical product, all of these features described above should be evaluated based on the safety and toxicity points of view. Aldehydes are strongly toxic, and sufficient care to avoid co-mixtures as an impurity is needed.

To eliminate the possible admixture of aldehydes as impurities, it is preferred that the formed Schiff base is once isolated as a solid, and then reduced. To employ bead-shaped chitosan as the base compound is considered to be preferable, because an intermediate compound formed with all of the aldehyde (the Schiff base compound) can be isolated, and can be reduced.

In order to eliminate aldehyde toxicity, it is preferred that the product obtained by reduction will be treated with dilute hydrochloric acid. Any Schiff base that has not been reduced is broken down by this procedure, which ensures the maximum level of safety of the obtained products.

This hydrochloric acid treatment makes long-term storage of the target compound to be possible, and makes recycling use possible. In the reduced compound, a number of the phenol groups are neutralized by sodium ions (—ONa). Phenol groups in this state are susceptible to oxidation by oxygen in the air, and turn brown when left to stand over time, and it has been verified that such browned samples exhibit reduced iron ion removal capability. To prevent this, it is preferable to store the phenol in —OH form. Hydrochloric acid treatment is necessary to accomplish this, and compounds obtained by such hydrochloric acid treatment are very good, and can being stored for extended periods. Further, adsorbed iron ions by the product can be removed all by dilute hydrochloric acid, and an H-type compound can be reused as an adsorbent, which makes the compounds very to be convenient on the economic stand of view.

Further, the hydrochloric acid treatment is also effective in removing excess reducing agent that was used in the process of synthesizing the compound. Through hydrochloric acid treatment, any unreacted reducing agent (e.g., NaBH$_4$) contaminated in the product can be eliminated in a short time. If hydrochloric acid is not used, the cleaning process will require time and effort. By carrying out hydrochloric acid treatment, the washing time can be dramatically shortened, and chelate compounds of high quality can be produced with good productivity.

Due to the hydrochloric acid treatment, the chelate compounds obtained thereby are converted to hydrochlorides, and through the procedure it is possible to provide various water-soluble chitosan chelate compounds capable of being developed into nanogels or films, highly safe and convenient water-insoluble chitosan chelate compounds, and other such novel chelate compounds which have a wide range of functions, and have a variety of forms.

EXAMPLE

Specific examples of the present invention are described below.

Example 1

In the present example, synthesis of chelate compounds was carried out using a commercially available chitosan. The chemical formula of the chitosan which was used is that shown in Formula 10, wherein $R_1=R_4=R_5=H$ and $R_2=R_3=OH$.

[Formula 10]

Into 100 mL of a 5% acetic acid solution (1/1 water-methanol) was dissolved 600 mg of 2,3-dihydroxybenzaldehyde, and 1.0 g of flake-shaped chitosan (purchased from Nacalai Tesque) was added to this. With the chitosan in a completely dissolved state, 2.2 g of sodium bicarbonate was added in small portions. After the all of the sodium bicarbonate had reacted, NaBH$_4$ was added in small portions (about 2 g). As a result, a large quantity of white precipitate that included slightly yellow crystals formed. After continuing to stir for a short while, the crystals were filtered. After being washed in methanol, the crystals were suspended in 100 mL of methanol, and NaBH$_4$ was added (about 0.5 g). After the crystals became completely white, the crystals were washed thoroughly in methanol, and dried over vacuum The dried compound obtained above was suspended in 100 mL of ethanol, 10 mL of concentrated hydrochloric acid was added thereto, and the suspension was stirred for one hour. The crystals were filtered by suction, washed thoroughly in ethanol, and dried over vacuum to obtain the target chelate compound (chelate compound A-1). Chelate compounds A-2 to A-9 were obtained by the same method.

Figure 1:
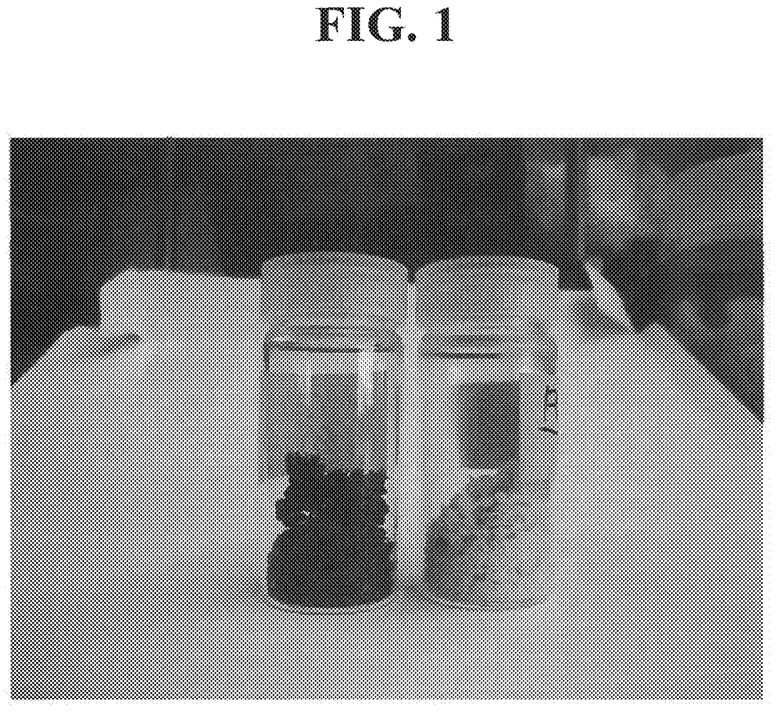
FIG. 1 is a photograph showing change in color of the chelate compound of Example 1.

For the chelate compounds obtained from flake-shaped chitosan, both the hydrochloride form and the non-hydrochloride form, were compared. As shown in FIG. 1, the non-hydrochloride form changed to brown color within a short time.

Example 2

A chelate compound (hydrochloride) was prepared in the same manner as Example 1, except for using chitosan having molecular weight of 54,000 as the base compound.

Example 3

A chelate compound (hydrochloride) was prepared in the same manner as Example 1, except for using chitosan having molecular weight of 35,000 as the base compound.

Example 4

In the present embodiment, a chelate compound was synthesized from a commercially available bead-shaped chitosan (CHITO PEARL BCW-3007™ from Fujibo Corp.) as the base compound, the chemical formula of the bead-shaped chitosan being that shown by Formula 11. In Formula 11, description of the crosslinking structure is omitted.

[Formula 11]

The bead-shaped chitosan was dried once. The dried bead-shaped chitosan (1.0 g) and 2,3-dihydroxybenzaldehyde (0.6 g) were added to water-methanol (1:4, 50 mL) and stirred for about one hour. The dried granular chitosan returned to its pre-drying granular state, and became yellow due to condensation with the aldehyde. The yellow-discolored granular chitosan was filtered by suction, and washed well with methanol (to eliminate the unreacted 2,3-dihydroxybenzaldehyde). The product was suspended in a methanol-water mixed solvent (4:1, 50 mL), and 3 g of sodium tetrahydroborate was added in small portions. The yellow granular chitosan turned white. After completing the addition, the product was left for one hour, filtered by suction, and washed thoroughly with water (to eliminate unreacted sodium tetrahydroborate). The granular chitosan thus obtained was added to a 1 N hydrochloric acid solution (50 mL) and stirred for one hour. The product obtained in this manner was filtered by suction, and washed with water, and then with methanol. The compound obtained (chelate compound B-1) was almost colorless.

Figure 2:
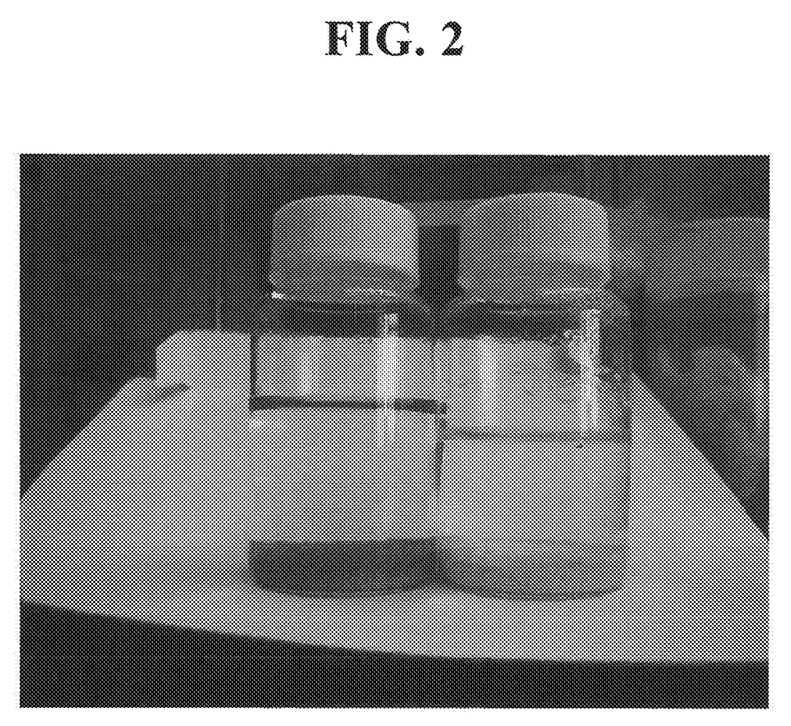
FIG. 2 is a photograph showing change in color of the chelate compound of Example 4.

In the same manner as in Example 1, both the hydrochloride form and the non-hydrochloride form of the obtained chelate compound were compared, and as shown in FIG. 2, the non-hydrochloride form changed to brown color within a short time.

Example 5

Figure 3:
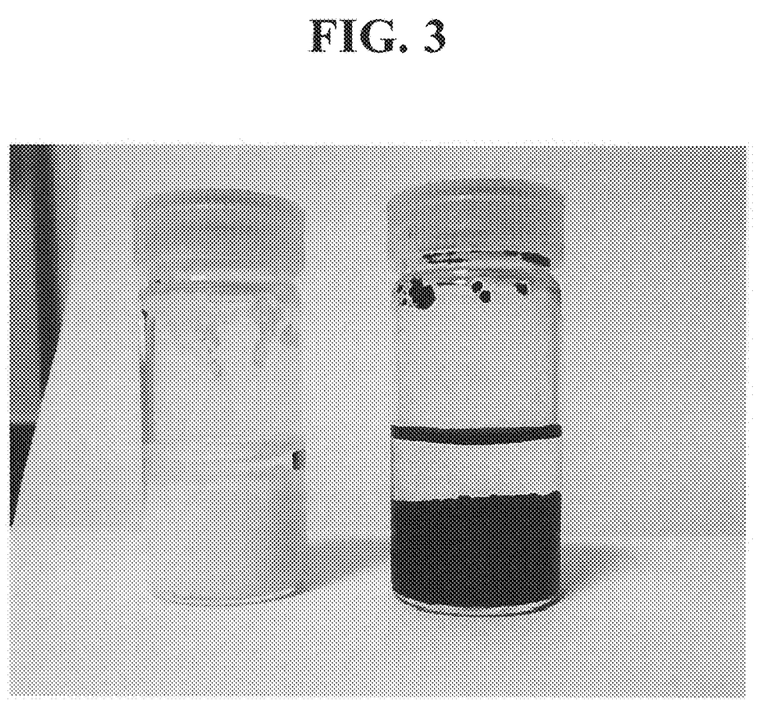
FIG. 3 is a photograph showing change in color of the chelate compound of Example 4, when prepared as an iron chelate.

The chelate compound (hydrochloride) obtained in Example 4 (chelate compound B-1) was suspended in 100 mL of water, K[Fe(ida) 2] (ida=iminodiacetic acid) (2.0) was added thereto, and the mixture was stirred for one hour. The black pearl-shaped compound obtained was filtered by suction, and washed thoroughly with water. An iron chelate was obtained. FIG. 3 is photographs showing difference in color between the chelate compound (hydrochloride) obtained in Example 4 (left) and one converted to an iron chelate (right). In the iron chelate, the compound changed to dark black due to incorporation of iron ions. The color of an iron chelate will differ depending on the chelate used. The iron chelate obtained had a very high ability to bind strongly with phosphate ions, diphosphate ions, polyphosphate ions, and thus it is apparent that these iron chelates show high ability to eliminate these ions from an aqueous solution.

Example 6

In the present embodiment, synthesis of a chelate compound was carried out using glucosamine as the base compound. Glucosamine hydrochloride (Wako Pure Chemical Industries, 2.15 g, 0.01 mol) was dissolved in an aqueous solution (10 mL) containing an equal amount of NaOH. 40 mL of a methanol solution containing 1.68 g (0.01 mol) of 3,4-dihydroxybenzaldehyde was added, a small amount of NaBH$_4$ (~300 mg) was added thereto, and the solution was reduced to small volume. After being left to stand for one hour, the solution was once filtered, and was adjusted to below pH 7 with dilute hydrochloric acid, and the target compound was obtained in the form of white precipitate by adding ethanol.

Test to Verify Functionality (1) When a hydrogel was prepared from the chelate compound A-6 obtained in Example 1, and was applied to the skin, senile keratoma was improved.

Figure 4:
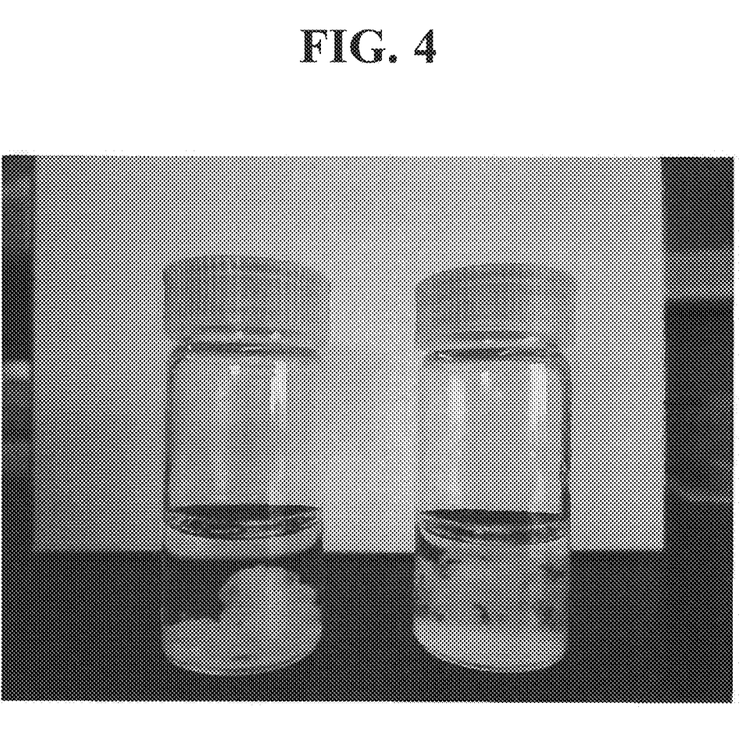
FIG. 4 is a photograph showing formation of precipitation by the chelate compound of Example 1 in the presence of phosphate ions.
Figure 5:
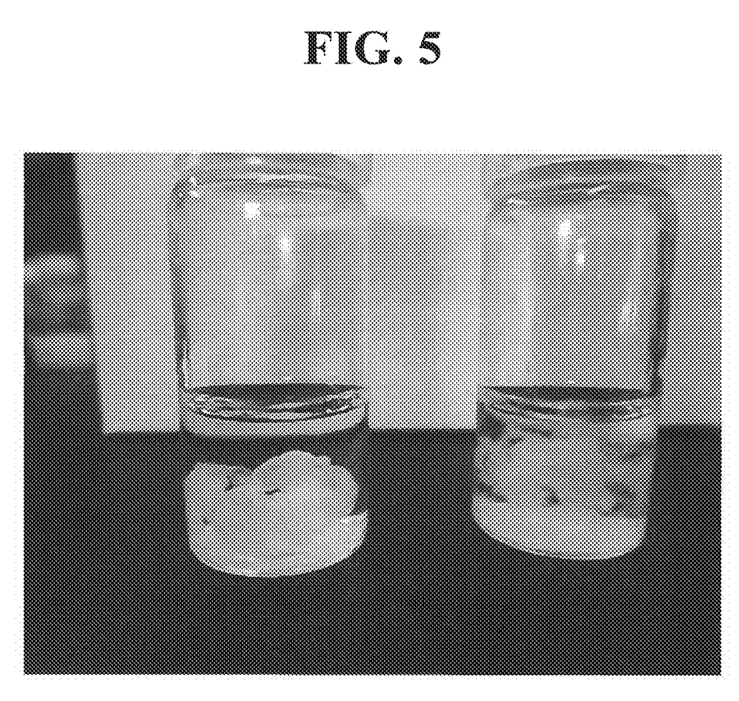
FIG. 5 is a photograph showing formation of precipitation by the chelate compound of Example 1 in the presence of another phosphoric acid.
Figure 6:
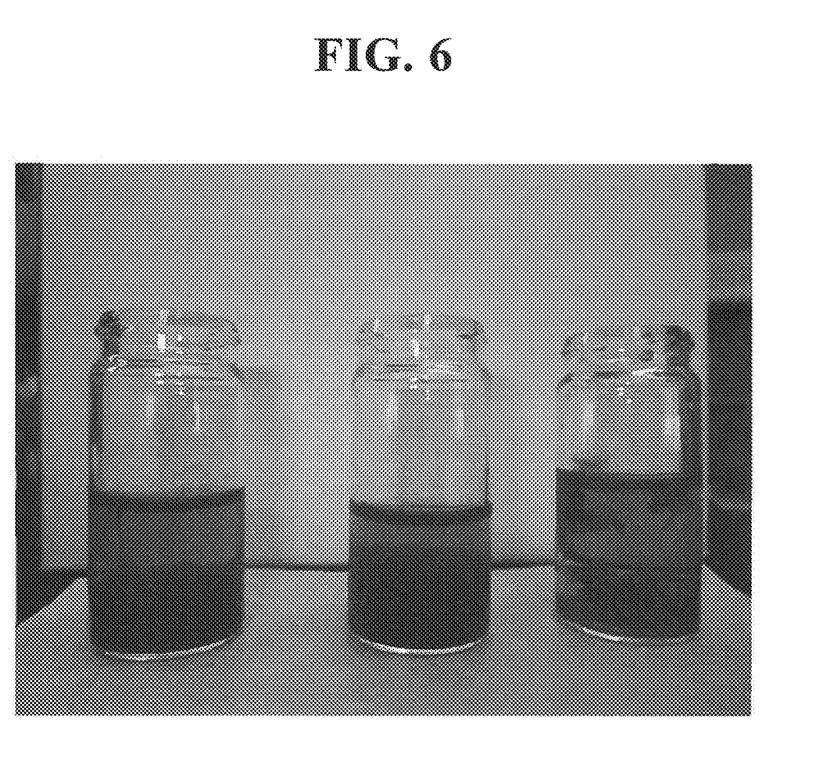
FIG. 6 is a photograph showing formation of precipitation by the chelate compound of Example 1 in the presence of dichromate ions.

(2) When a hydrogel was prepared from the chelate compound (hydrochloride) obtained in Example 1, and added to a solution containing phosphate ions, a precipitate formed as shown in FIG. 4, demonstrating that the compound can be used as an agent for eliminating phosphate ions (in the drawing, the left is chelate compound A-6, and the right is chelate compound A-9). The chelate compound A-6 obtained in Example 1 demonstrated similar effects with diphosphate (left) and polyphosphate (right) as shown in FIG. 5. Further, hydrogels of the chelate compounds (hydrochlorides) also caused bichromate ions to precipitate, as shown in FIG. 6 (in the drawing, the left side is chelate compound A-6, the center is chelate compound A-9, and the right side is chelate compound A-2).

Figure 7:
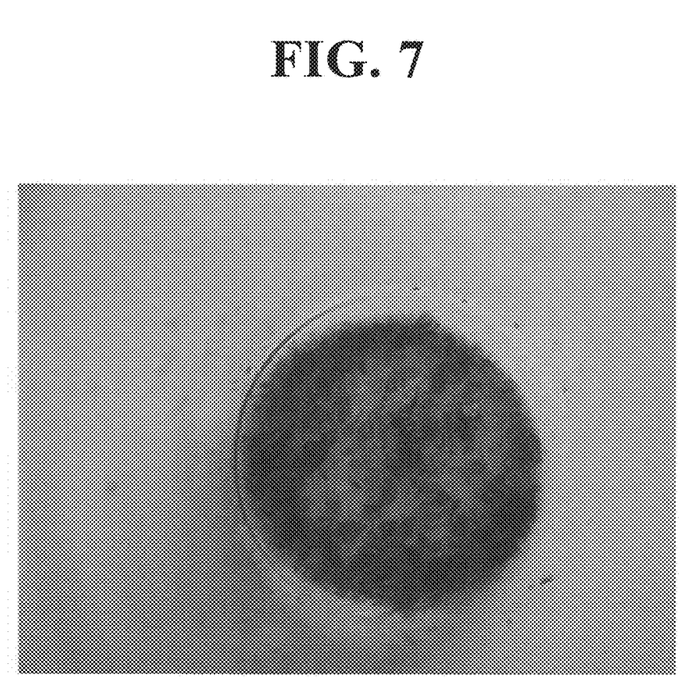
FIG. 7 is a photograph showing formation of nanogel due the chelate compound of Example 1.

(3) FIG. 7 shows a nanogel formed by the chelate compound (hydrochloride) obtained in Example 1 (chelate compound A-6). When an iron solution was added to an aqueous solution of the chelate compound (hydrochloride) obtained in Example 1 (chelate compound A-6), the red color of the iron chelate was not uniform, and became mottled, indicating of the nanogel formation.

Figure 8:
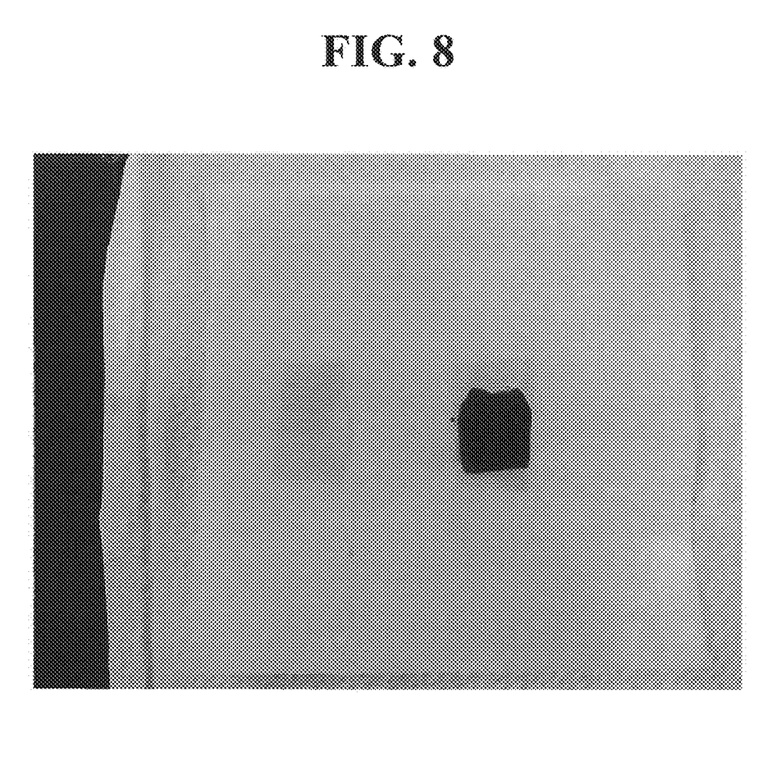
FIG. 8 is a photograph showing iron detection by a film of the chelate compound of Example 1.

(4) FIG. 8 shows a film of the chelate compound (hydrochloride) obtained in Example 1 (chelate compound A-2) (left), and the film when immersed in an iron solution (right). The obtained film reacts sharply with the iron ions, and can therefore be used to detect iron ions.

The invention claimed is:

1. A chelate compound, wherein
a phenol derivative bound with a base compound having amino groups, at least some of the amino groups taking the form of a halide salt,
the base compound has a glucosamine structure
the base compound is chitosan,
the phenol derivative is on at least the surface of water-insoluble bead-shaped chitosan, the amino groups on at least the surface of the bead-shaped chitosan being halide salts, and
the chelate compound has a structure indicated by Formula 2, and

[Formula 2]

in the Formula 2, at least one of $R_1$, $R_2$, $R_3$, $R_4$ and $R_5$ is a hydroxyl group, the others being any group selected from hydrogen, hydroxyl groups, carboxyl groups, and alcohol groups.

* * * * *